United States Patent [19]

Yoshida

[11] 4,437,115

[45] Mar. 13, 1984

[54] OBJECT AND INSPECTION SYSTEM

[75] Inventor: Hajime Yoshida, Tokyo, Japan

[73] Assignee: Hajime Industries Ltd., Japan

[21] Appl. No.: 396,166

[22] Filed: Jul. 8, 1982

Related U.S. Application Data

[63] Continuation-in-part of Ser. No. 112,839, Jan. 17, 1980, abandoned.

[30] Foreign Application Priority Data

Jan. 25, 1979 [JP] Japan .................................. 54-7930

[51] Int. Cl.³ ............................................. H04N 7/18
[52] U.S. Cl. ..................................... 358/106; 358/183
[58] Field of Search ....................... 358/106, 105, 183; 250/562, 563, 572; 356/237, 430, 431

[56] References Cited

U.S. PATENT DOCUMENTS

| 3,580,997 | 5/1971 | Webb | 358/106 |
| 3,740,467 | 6/1973 | Kubo et al. | 358/106 |
| 3,916,439 | 10/1975 | Lloyd et al. | 358/106 |
| 4,017,680 | 4/1977 | Anderson et al. | 358/183 |
| 4,163,991 | 8/1979 | Burrig | 358/106 |
| 4,168,510 | 9/1979 | Kaiser | 358/183 |

Primary Examiner—Joseph A. Orsino, Jr.

[57] ABSTRACT

An object inspection system, upon detecting the presence of a flaw in a video signal from a television camera cyclically varies the video corresponding to the flaw so that an image displayed on a television monitor is correspondingly periodically brightened or flickered to identify the location of the defect to an operator and to alert the operator to the presence of such defect.

4 Claims, 13 Drawing Figures

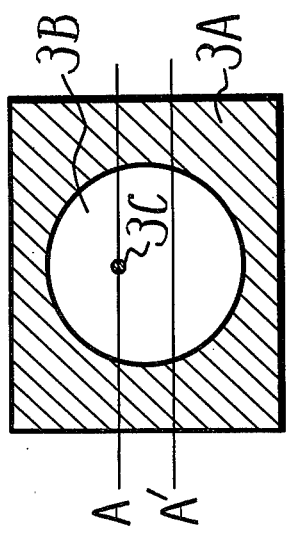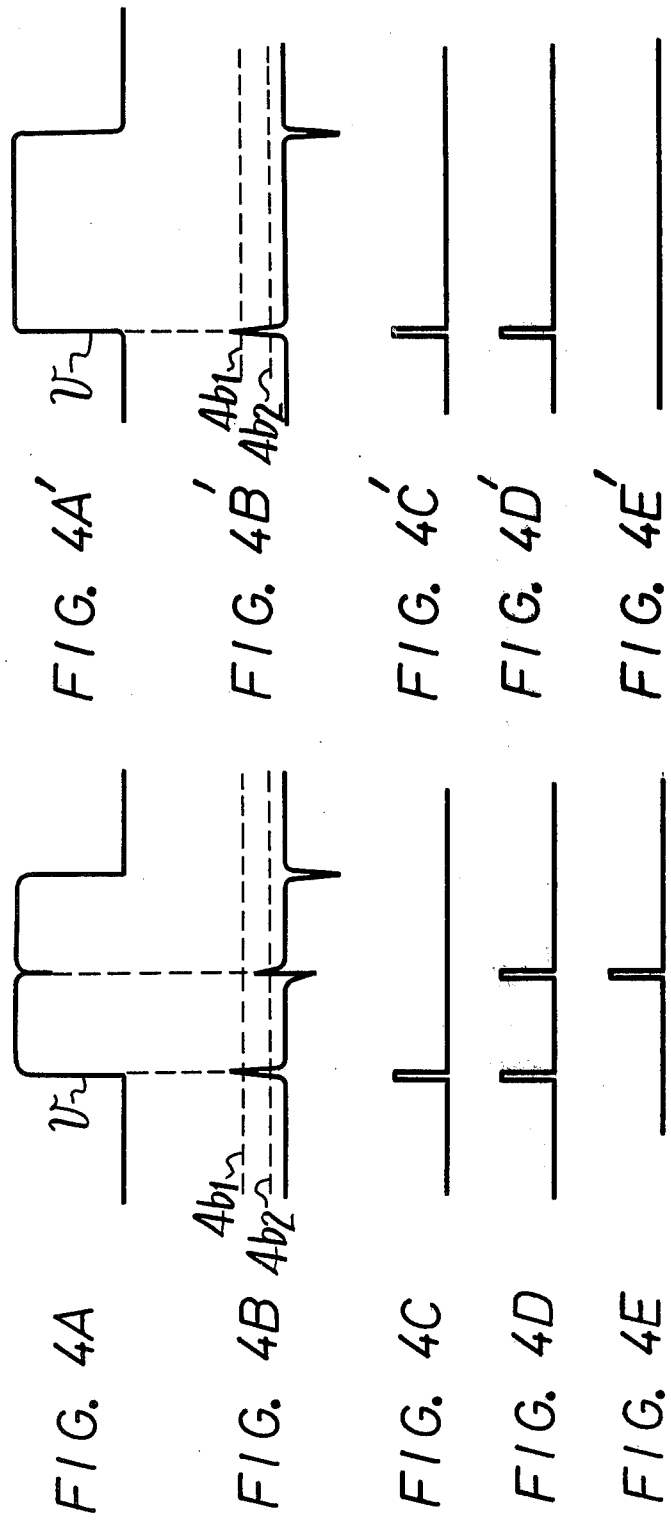

OBJECT AND INSPECTION SYSTEM

The present application is a continuation-in-part of co-pending U.S. patent application Ser. No. 112,839 filed Jan. 17, 1980, abandoned concurrent with the filing hereof.

BACKGROUND OF THE INVENTION

The present invention relates generally to object inspection systems and, more particularly, to object inspection systems utilizing a video signal derived from an electrooptical sensor such as a television camera, solid state photo sensor or matrix array.

Object inspection systems have employed pattern recognition in which a video signal from a tv camera viewing the object to be inspected is processed in a computer to detect the existence of irregularities on an inspected object. Although such systems can detect even very small irregularities, the problem remains to inform a human operator about the location of such problems by isolating them on a television monitor. This problem becomes especially difficult when the irregularities or flaws are very small.

OBJECTS AND SUMMARY OF THE INVENTION

Accordingly, it is an object of the present invention to provide an object inspection system which overcomes the drawbacks of the prior art.

A further object of the present invention is to provide an object inspection system in which human isolation of the defect or flaw is enhanced.

It is a further object of the invention to provide an object inspection system wherein an image of the object is produced on a monitor screen and areas of the monitor image containing an irregularity or flaw are flickered or blinked in order to aid the operator in isolating the areas containing the irregularity or flaw.

According to an aspect of the present invention, there is provided an object inspection system for sensing and indicating defects in an object, comprising an image sensing device effective to produce a video signal representing the object, a monitor television receiver for reproducing an image from the video signal, a processor including at least one of a differentiation circuit and a level comparator, the processor being effective to produce a first signal when the video represents a good portion of the object and a second signal when the video represents a not good portion of the object, a modulator responsive only to the second signal to produce a modulated signal, and a signal mixer effective to mix the video signal with the modulated signal and to cause blinking in portions of the image corresponding to the not good portions of the object whereby the not good portions of the object are clearly determined from the blinking portions of the image.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 3 is a view of a monitor screen imaging an object to be inspected with two scan lines, one of which contains a flaw or irregularity.

FIGS. 4A through 4E are curves to which reference will be made in describing the process of isolating the flaw in one of the scan lines of FIG. 3.

FIGS. 4A' through 4E' are curves to which reference will be made in describing processing of a scan line in FIG. 3 which does not contain a flaw or irregularity.

DETAILED DESCRIPTION OF THE PREFERRED EMBODIMENT

Figure 1:
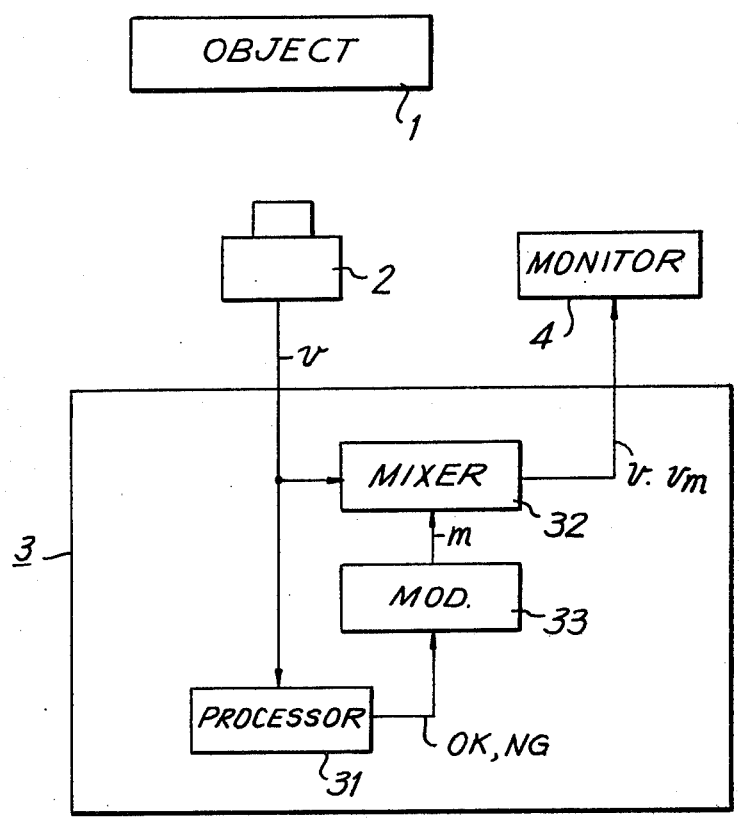
FIG. 1 is a simplified block diagram of an embodiment of the present invention.

Referring to FIG. 1, an electrooptical image sensor 2 which may be of any convenient type such as, for example, a television camera, solid state imaging device such as a CCD, or a matrix array produces a video signal v of an object. The video signal v is processed in an object inspection apparatus 3 to determine whether or not one or more irregularities or flaws exist an object 1.

Object 1 may be of indefinite extent in one direction such as, for example, a web of material completely filling the field of view of image sensor 2 in at least one dimension or, alternatively, object 1 may consist of one or more discrete objects. Although not completely necessary for the practice of the invention, in the description which follows, it will be assumed that object 1 has a single level of apparent brightness over its entire surface viewed by image sensor 2 and that any discrete departure from this uniform level of apparent brightness represents a flaw or irregularity in the surface which should be drawn to the attention of an operator.

Video signal v is applied to a processor 31 and to a mixer 32 in object inspection apparatus 3. Processor 31 determines whether or not the image contains irregularities. During times that processor 31 receives a video signal which does not contain irregularities, an OK signal is produced and applied to a modulator 33. When an irregularity or flaw is detected in the video signal v by processor 31, processor 31 produces a not good signal NG which is applied to modulator 33. In response to its two possible inputs, modulator 33 produces a modulation signal m in response to a not good input NG which is applied to mixer 32. The modulation signal m may be a periodic pulsed signal which is applied to that portion of the video signal v which contains the irregularity or flaw. The pulsed modulation signal m thereby darkens and brightens the video signal in the affected area to produce a modulated video signal vm in these regions which is applied to monitor 4. By appropriate selection of the pulse frequency of modulation signal m, the operator's attention is drawn to the flaw by the flickering or periodic brightening and darkening of the screen monitor 4 in the area containing the flaw. A frequency of, for example, two pulses per second may be employed with an appropriately chosen duty ratio selected to best capture the attention of an observer. The periodic flickering or brightening and darkening of the flaw or irregularity makes it possible for the observer to pick out the object 1 containing the flaw or to easily locate the area of object 1 containing the flaw for selection or correction.

Figure 2:
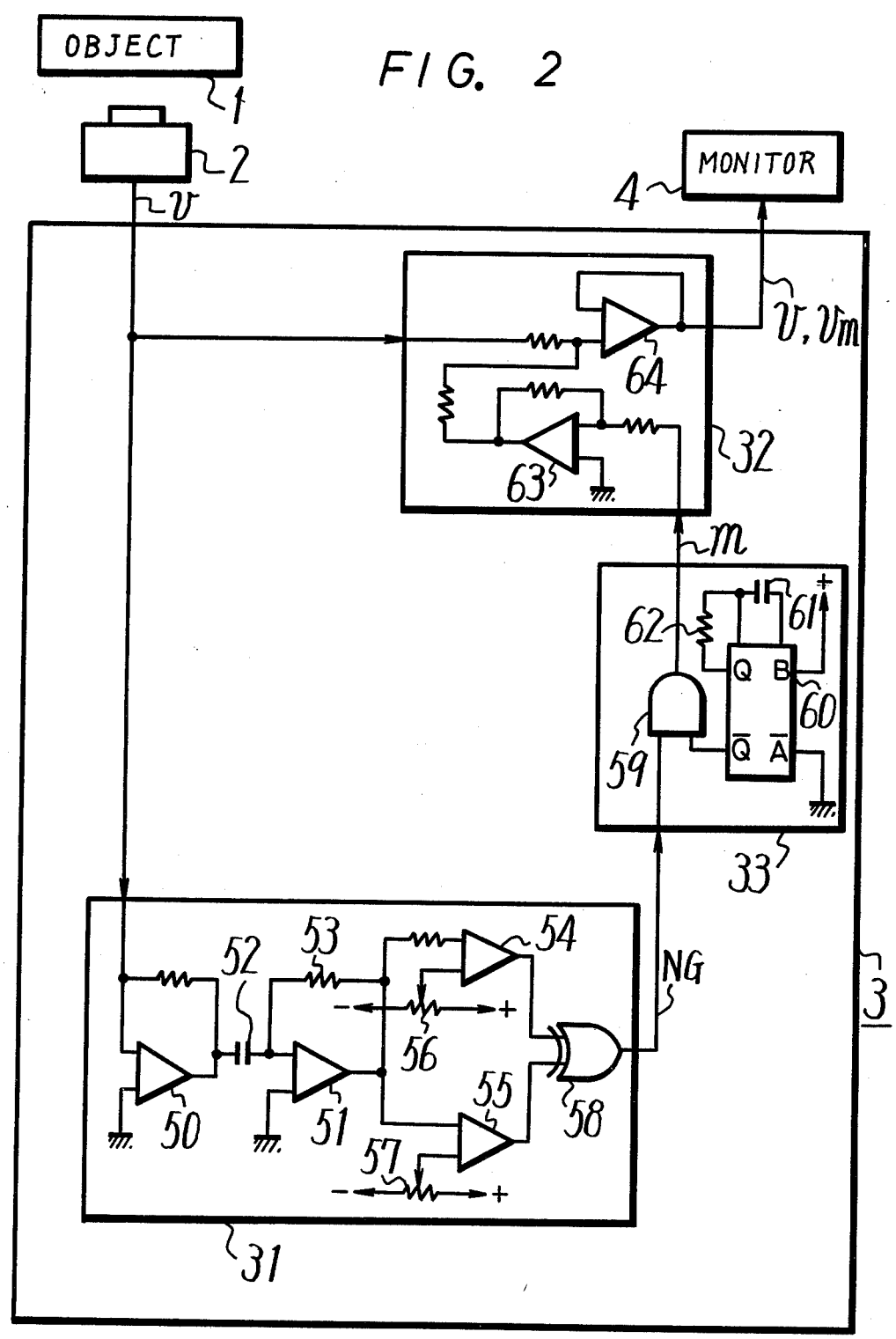
FIG. 2 is a more detailed diagram of the embodiment of FIG. 1, showing the contents of the object inspection apparatus.

Referring now to FIG. 2, processor 31 is seen to contain a conventional video amplifier 50 for amplifying video signal v and applying it to a differentiating circuit consisting of capacitor 52, operational amplifier 51 and feedback resistor 53. The time constant of capacitor 52 and feedback resistor 53 is selected to provide positive-and negative-going spikes as the video signal passes from dark to bright areas and vice-versa.

The differentiated signal from the differentiating circuit is applied to inputs of comparators 54 and 55. Different reference voltages are selected for comparators 54 and 55 by variable resistors 56 and 57. Outputs of comparators 54 and 55 are applied to inputs of an exclusive OR gate 58. As is well known, an exclusive OR gate produces a low or zero output when its inputs are the same (either high or low) and produces a one or high output when its inputs are different. The outputs of comparators 54 and 55 are different only during the time that the signal from the differentiating circuit is above the reference voltage set by one of variable resistors 56 and 57 and below the voltage set by the other.

Referring now to FIG. 3, a video screen 3A of monitor 4 is shown with a circular bright object 3B illustrated corresponding to object 1 of FIGS. 1 and 2. A horizontal scan line A passes through the dark and bright regions of target screen 3A and crosses over a dark flaw or irregularity 3C. A second horizontal scan line A' crosses target screen 3A at a region which is correct and does not contain an irregularity or flaw.

Referring to FIGS. 4A through 4E, video signal v is shown in FIG. 4A in response to the scanning line A containing irregularity or flaw 3C. It will be noted that as the scan line passes from the dark background to the bright image 3B of object 1, the video suddenly rises from a low to a high level. At an intermediate point at which flaw 3C is scanned, a negative excursion is produced in video signal v. Finally, at the transition from image 3B of object 1 to the darker background on target screen 3A, the video signal drops to its lower level.

The output of operational amplifier 51 of FIG. 2 is shown in FIG. 4B. It will be noted that this output provides a positive-going spike at the left edge of object 3B, a negative-going spike followed immediately by a positive-going spike at flaw 3C and a negative-going spike at the right edge of object 3B. Dashed lines $4b_1$ and $4c_2$ represent the thresholds applied to comparators 54 and 55 from variable resistors 56 and 57 respectively. It will be noted that both thresholds are exceeded at the transition from the dark background on to object 3B. FIGS. 4C and 4D illustrate the outputs of comparators 54 and 55 respectively at this time. As flaw 3C is scanned, assuming that flaw 3C is small enough that the differentiating circuit has not yet recovered before the flaw is past, the positive-going portion of the differentiated signal exceeds threshold $4b_2$ but does not exceed threshold $4b_1$. Thus, an output is generated from comparator 55 as indicated in FIG. 4D while no corresponding output is generated by comparator 54 as shown in FIG. 4C.

The output of exclusive OR gate 58 is shown in FIG. 4E. At the left edge of image 3B, both thresholds are exceeded at approximately the same time for approximately the same duration. Thus, both inputs to exclusive OR gate remain approximately the same throughout the period, therefore, the output of exclusive OR gate 58 at the left edge of image 3B remains low or zero. However, when passing over the flaw, since the differentiated signal exceeds only threshold $4b_2$ and does not exceed threshold $4b_1$, only the output of comparator 55 is high and therefore the two inputs to exclusive OR gate 58 are different. This produces an output signal as shown in FIG. 4E which corresponds to the not good signal NG from processor 31.

In contrast, FIGS. 4A' through 4E' illustrate the situation while scanning line A' in FIG. 3 which does not include a flaw 3C. That is, the positive-going signal at the left edge of image 3B as before produces no output signal. Since no flaw 3C exists in the middle of the video signal, there is no situation under which one of the thresholds is exceeded and the other is not. Consequently, no signal is produced by exclusive OR gate 58 as indicated in FIG. 4E'.

Returning now to FIG. 2, modulator 33 is seen to contain an AND gate 59 receiving the output of processor 31 at one of its inputs. An oscillator 60 whose frequency is determined by a capacitor 61 and resistor 62 provides an oscillating signal, preferably a square-wave, to the second input of AND gate 59. In the absence of a flaw in the image, the signal applied to AND gate 59 from exclusive OR gate 58 maintains AND gate 59 inhibited. Thus, the output of AND gate 59 remains constant. Alternatively, when a flaw is detected in processor 31, the not good signal NG applied to an input of AND gate 59 enables AND gate 59 to pass the pulse signal from oscillator 60 as a modulation signal m to mixer 32. An operational amplifier 63 in mixer 32 receives the modulation signal m whose output is applied through a resistor to an input of an operational amplifier 64. The video signal v is applied through a resistor to the same input of operational amplifier 64. The two resistors, one receiving the amplified modulation signal m and the other receiving the video signal v add these two signals and provide the resulting sum to the input of operational amplifier 64. Operational amplifier 64 is connected as a unity gain current amplifier which outputs either the video signal v when no flaw is detected or the modulated video signal vm in the area where a flaw is detected. The sequential brightening and darkening of the image on monitor television receiver 4 corresponding to the flaw alerts the operator to the existence and location of the flaw.

Although not shown in the figures, oscillator 60 may be synchronized to the frame rate of monitor television receiver 4. For example, oscillator 60 may be arranged to provide an output for a predetermined number of television frames with an intervening period of no output. For example, it may be desirable to brighten the television for one third of the frames and to return it to the normal brightness for two thirds of the frames. If a flicker rate of two per second is desired at this duty ratio in a television system employing thirty frames per second, oscillator 60 may be arranged to brighten the image of flaw 3C for five successive frames and to leave the next ten successive frames unbrightened and to continue this sequence as long as a flaw is detected. This produces a flicker rate of two per second with a one third duty ratio.

Besides or instead of displaying the flickering portion of a television signal when a flaw is detected, the flaw detection herein may be employed to actuate a reject mechanism for rejecting a defective object or to generate an alarm to inform the operator of the existence of the defective object. It would be clear to one skilled in the art that the not good signal NG from processor 31 may be employed to trigger any operation of this type. Alternatively, it may be desirable to produce a signal which indicates that the object being displayed is good. Conventional logic circuitry (not shown) may be employed to determine whether a flaw is detected any-where during the scanning of the object and, if no flaw is detected, the object can be considered a good object.

If the object being inspected is a nominally plain sheet of material such as paper or metal instead of a discrete object such as a white bottle cap as in the example in FIG. 3, the detection of black or dark spots can be performed without employing comparator 54 or exclusive OR gate 58 of FIG. 4. Instead, the output of comparator 55 may be employed directly to indicate the existence of a flaw and to produce the not good signal NG.

The differentiation circuit and comparators of the present invention may be replaced by a processor such as those disclosed in U.S. Pat. Nos. 4,302,773 and 4,277,802 by the present applicant. In addition, a comparator and one-shot multi-vibrator may be employed instead of processor 31 without departing from the spirit or scope of the present invention.

Having described specific embodiments of the invention with respect to the accompanying drawings, it is to be understood that the invention is not limited to those precise embodiments, and that various changes and modifications may be effected therein by one skilled in the art without departing from the scope or spirit of the invention as defined in the appended claims.

I claim:

1. An object inspection system for sensing and indicating defects in an object, comprising:
    an image sensing device effective to produce a video signal representing said object;
    a monitor television receiver for reproducing an image from said video signal;
    a processor including at least one of a differentiation circuit and a level comparator, said differentiation circuit being effective to produce an output having a characteristic related to a change in said video signal, said level comparator including means signal effective for producing a first signal when said characteristic represents a good portion of said object and a second signal when said characteristic represents a not good portion of said object;
    a modulator responsive only to said second signal to produce a modulated signal; and
    a signal mixer effective to mix said video signal with said modulated signal and to cause blinking in portions of said image corresponding to said not good portions of said object whereby said not good portions of said object are clearly determined by said blinking portions of said image.

2. An object inspection system according to claim 1, wherein said at least one differentiating circuit includes means effective for differentiating said video signal to produce a differentiated signal, and said level comparator includes means responsive to said differentiated signal exceeding a predetermined value for producing said second signal.

3. An object inspection system according to claim 1 or 2, wherein said differentiating circuit includes means effective for differentiating said video signal to produce a differentiated signal, and said level comparator includes means responsive to said differentiated signal exceeding a first predetermined value and remaining less than a second predetermined value for producing said second signal.

4. An object inspection system according to claim 1, wherein said modulator includes an oscillator, said oscillator being effective to produce a periodic signal and said modulator further includes gating means responsive to the simultaneous presence of both said periodic signal and said second signal to produce said modulated signal.

* * * * *